United States Patent [19]
Saito et al.

[11] Patent Number: 4,818,429
[45] Date of Patent: Apr. 4, 1989

[54] CYCLOHEXYLPHENYLPYRIDAZINES

[75] Inventors: Shinichi Saito; Takashi Inukai; Hiromichi Inoue; Kazutoshi Miyazawa; Kouji Ohno, all of Kanagawa, Japan

[73] Assignee: Chisso Corporation, Osaka, Japan

[21] Appl. No.: 95,111

[22] Filed: Sep. 11, 1987

[30] Foreign Application Priority Data

Sep. 11, 1986 [JP] Japan ................... 61-214471

[51] Int. Cl.$^4$ ................... C09K 19/34; C09K 19/52; C07D 237/00; C07D 237/02
[52] U.S. Cl. ................... 252/299.61; 252/299.01; 252/299.5; 350/350 R; 350/350 S; 544/224; 544/239
[58] Field of Search ............ 252/299.61, 299.01, 252/299.5; 250/250 R, 350 S; 544/239, 224

[56] References Cited

U.S. PATENT DOCUMENTS

| | | | |
|---|---|---|---|
| 4,452,718 | 6/1984 | Schadt et al. | 252/299.61 |
| 4,565,425 | 1/1986 | Petrzilka et al. | 252/299.61 |
| 4,595,521 | 6/1986 | Petrzilka et al. | 252/299.61 |
| 4,657,695 | 4/1987 | Saito et al. | 252/299.61 |
| 4,676,604 | 6/1987 | Petrzilka | 252/299.61 |
| 4,713,197 | 12/1987 | Eidenschink et al. | 252/299.61 |
| 4,723,005 | 2/1988 | Hutma-Ba et al. | 252/299.61 |

FOREIGN PATENT DOCUMENTS

| | | | |
|---|---|---|---|
| 174541 | 3/1986 | European Pat. Off. | 252/299.61 |
| 3515373 | 11/1986 | Fed. Rep. of Germany | 252/299.61 |
| 8606401 | 11/1986 | PCT Int'l Appl. | 252/299.61 |

OTHER PUBLICATIONS

Schubert, H., Wiss. Z. Univ. Halle XIX'70 M, H.5, 5.1–18.
Demus, D., et al., Flussile Fristalle Intabellen, Veb Deutscher Verlag fur Grundstoffimustrie, Leifzig, pp. 259–260 (1974).
Demus, D., et al., Flussile Fristalle Intabellem II, Veb Deutscher Verlag fur Grundstoffimustrie, Leipzig, pp. 344–400 (1984).
Gray, G. W., et al., Liquid Crystals & Plastic Crystals, vol. 1, John Wiley & Sons, Ltd., N.Y., pp. 142–143 (1974).
C.A. 102: 78810h (1985).
C.A. 106: 166738d (5/18/87).
C.A. 104: 216956e (6/16/86).
C.A. 104: 139769s (4/21/86).

Primary Examiner—Teddy S. Gron
Attorney, Agent, or Firm—Wenderoth, Lind & Ponack

[57] ABSTRACT

A compound useful as a component constituting ferroelectric liquid crystal display elements and a liquid crystal composition containing the same are provided, which compound is expressed by the formula

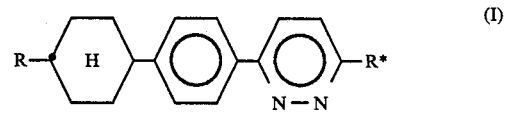

(I)

wherein R represents a linear or branched chain alkyl group of 1 to 20 carbon atoms and R* represents an optically active alkyl group, alkoxy group, alkoxyalkyl group, alkoxyalkoxy group, alkanoyloxyalkyl group, alkanoyloxyalkoxy group, halogenated alkyl group or halogenated alkoxy group each of 2 to 20 carbon atoms.

4 Claims, No Drawings

CYCLOHEXYLPHENYLPYRIDAZINES

BACKGROUND OF THE INVENTION

1. Field of the Invention

This invention relates to a novel liquid crystal compound. More particularly it relates to a chiral liquid crystal compound having an optically active group and a chiral liquid crystal composition containing the same.

The liquid crystal compound referred to herein includes not only substances which liquid crystal state can be observed by themselves, but also those which liquid crystal state cannot be observed by themselves and nevertheless which have a similar chemical structure to those of liquid crystal compounds and are suitable as a component constituting liquid crystal compositions.

2. Description of the Related Art

At present, TN (Twisted Nematic) mode display has been most broadly employed for liquid crystal display elements. This TN liquid crystal display has many advantages such as low driving voltage, small power consumption, etc. However, the elements are inferior in the aspect of response rate to emissive mode display elements such as those of cathode ray tube, electroluminescence, plasma display, etc. A new TN mode display element having the twist angle increased from conventional 90° up to 180°~270° has also been developed, but it is still inferior in the response rate. As described above, various efforts for improvement has been made, but such efforts have not yet fruitful. On the other hand, a new display mode using ferroelectric liquid crystals has a possibility of notably improving the response rate (Clark et al; Applied Phys. lett., 36, 899 (1980)). This mode is directed to a method of making use of chiral smectic phases such as chiral smectic C phase (hereinafter abbreviated to SC*) exhibiting ferroelectric properties. It has been known that phases exhibiting ferroelectric properties are not limited only to SC* phase, but chiral smectic F, G, H, I, etc. phases also exhibit ferroelectric properties. However, for making practical use of ferroelectric liquid crystal display elements, a number of characteristics have been required for liquid crystal materials used therefor.

SUMMARY OF THE INVENTION

The object of the present invention is to provide a compound useful as a constituent of liquid crystal materials for such ferroelectric liquid crystal display elements.

The present invention resides in a compound expressed by the formula

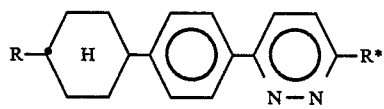

wherein R represents a linear or branched chain alkyl group of 1 to 20 carbon atoms and R* represents an optically active alkyl group, alkoxy group, alkoxyalkyl group, alkoxyalkoxy group, alkanoyloxyalkyl group, alkanoyloxyalkoxy group, halogenated alkyl group or halogenated alkoxy group each of 2 to 20 carbon atoms, and a liquid crystal composition containing the same.

DETAILED DESCRIPTION OF PREFERRED EMBODIMENTS

While the compound of the formula (I) may include either that which exhibit SC* phase or that which exhibit no SC* phase, it has the following specific features:

A first specific feature of the compound of the present invention consists in that it has a large negative dielectric anisotropy value.

As the display mode using ferroelectric liquid crystals, two modes have been considered. One mode is of a birefringence type using two sheets of polarizers and the other is of a guest-host type using dichroic dyestuffs. Since SC* phase has a spontaneous polarization, molecules are inverted around the helical axis as a rotating axis by inverting the polarity of the impressed voltage. When a liquid crystal composition having SC* phase is filled in a liquid crystal display cell subjected to an aligning treatment so that the liquid crystal molecules can be arranged in parallel to the electrode surface; the cell is placed between two sheets of polarizers arranged so that the director of the liquid crystal molecules can be in parallel to the other polarization plane; and a voltage is impressed to invert the polarity, then a bright field of vision and a dark field of vision determined by the opposed angle of the polarizers are obtained. On the other hand, in the case of operation according to the mode of guest-host type, it is possible to obtain a bright field of vision and colored field of vision which are determined by the arrangement of polarization plane, by inverting the polarity of impressed voltage.

In either of these modes, since an alternating square wave is impressed as the driving method, it is preferred that the dielectric anisotropy value be negative. The reason is that if a display element is prepared using a ferroelectric liquid crystal composition having a positive dielectric anisotropy value, liquid crystal molecules rise due to impression of the alternate square wave; hence it is difficult to obtain a display element having a high quality. When the compound of the formula (I) of the present invention is added in a suitable quantity to such a ferroelectric liquid crystal compound or composition having a positive dielectric anisotropy value, it is possible to convert the latter into a composition having a negative dielectric anisotropy value which is suitable to ferroelectric liquid crystal display.

Next, a second specific feature of the present invention consists in that the optical anisotropy value is small. As the display mode using ferroelectric liquid crystals, the two methods are considered as described above. In the birefringence mode display using two sheets of polarizers between the above two, the above second specific feature is very effective.

As to the birefringence mode display element, it has been considered most desirable that the product of the optical anisotropy value by the cell thickness (μm) be 0.25. At present, however, the cell thickness of elements led from the optical anisotropy values of well known ferroelectric liquid crystal compositions is 2 μm. It is very difficult to prepare elements of such a cell thickness without any thickness unevenness. Whereas since the compound of the formula (I) of the present invention has a cyclohexane ring, its optical anisotropy value is small. Thus when the compound of the present invention is added in a suitable quantity to a compound or composition having a large optical anisotropy value, it is possible to sufficiently reduce the optical anisotropy value of the composition. As a result, it is possible to more increase the cell thickness of elements; hence it is possible to prepare cells which can correspond enough to current cell preparation technique.

A third specific feature of the present invention consists in that the compound of the formula (I) of the present invention has a low viscosity. Thus when the compound of the formula (I) of the present invention is added in a suitable quantity to a liquid crystal compound or composition, it is possible to constitute a ferroelectric liquid crystal composition for display elements having a high response rate.

In the case of constituting a chiral smectic liquid crystal composition, mixing of the compound of the formula (I) with other chiral or achiral smectic liquid crystal compound and/or composition makes it possible to prepare a liquid crystal composition exhibiting SC* phase.

In addition, the racemic modification corresponding to the compound of the formula (I) may be similarly prepared by using a raw material for the racemic modification in place of the optically active compound in the preparation of the optically active compound (I) mentioned later, and in this case, the resulting racemic modification exhibits almost the same phase transition points as those of the compound of the formula (I). Namely, when the optically active compound exhibits SC* phase, the racemic modification exhibits SC phase in place of SC* phase, while when the optically active compound exhibits SA phase, the racemic modification also exhibits SA phase. When any of these is added to the optically active compound (I), they may be used for adjusting the pitch of the chiral smectic phase. Further, since the compound of the formula (I) has an optically active carbon atom, it has a capability of inducing a twisted structure by adding it to a nematic liquid crystal. Nematic liquid crystals having a twisted structure i.e. chiral nematic liquid crystals do not form the so-called reverse domain of TN mode display elements; hence it is possible to use the compound of the formula (I) as an agent for preventing the reverse domain from forming.

Next, preparation of the compound of the formula (I) will be described. The compound of the formula (I) may be prepared as in the following scheme:

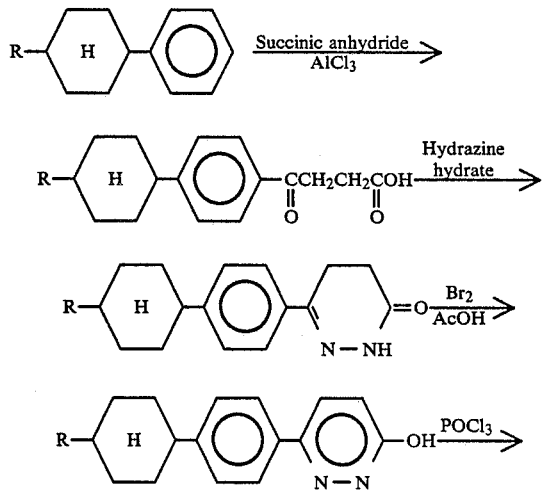

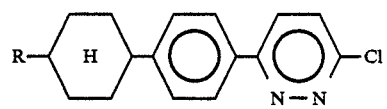

(a) In the case R* represents an alkyl group or an alkoxyalkyl group:

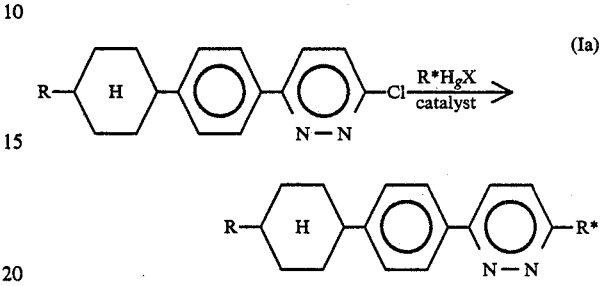

wherein X represents chlorine, bromine or iodine, and as the catalyst, Ni compounds are preferred and $NiCl_2(PPh_3)_2$, $NiCl_2(dppp)$ (dppp: bis(diphenylphosphino)-propane), etc. are particularly preferred.

(b) In the case where R* represents an alkanloylalkyl group:

R* is expressed by the formula

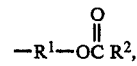

and $POR^1MgX$ as its precursor is reacted as follows:

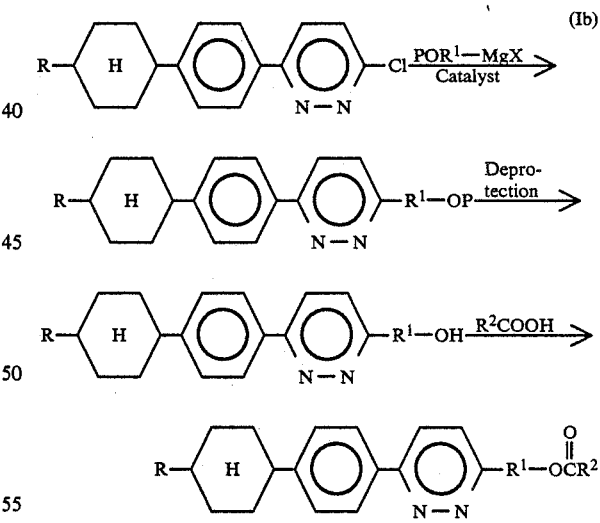

wherein X and the catalyst are the same as the above, $R^1$ represents an alkylene group and $R^2$ represents an alkyl group, but either one or both of these are an optically active group, and P represents a protective group such as 2-tetrahydropyranyl, methoxymethyl, 1-ethoxyethyl, 1-ethoxy-1-methylethyl, etc.; further, "deprotection" refers to removal of protective group.

(c) In the case where R* represents a halogenated alkyl:

R* is expressed by $-R^1-Hal$, and $POR^1MgX$ as its precursor is reacted as follows:

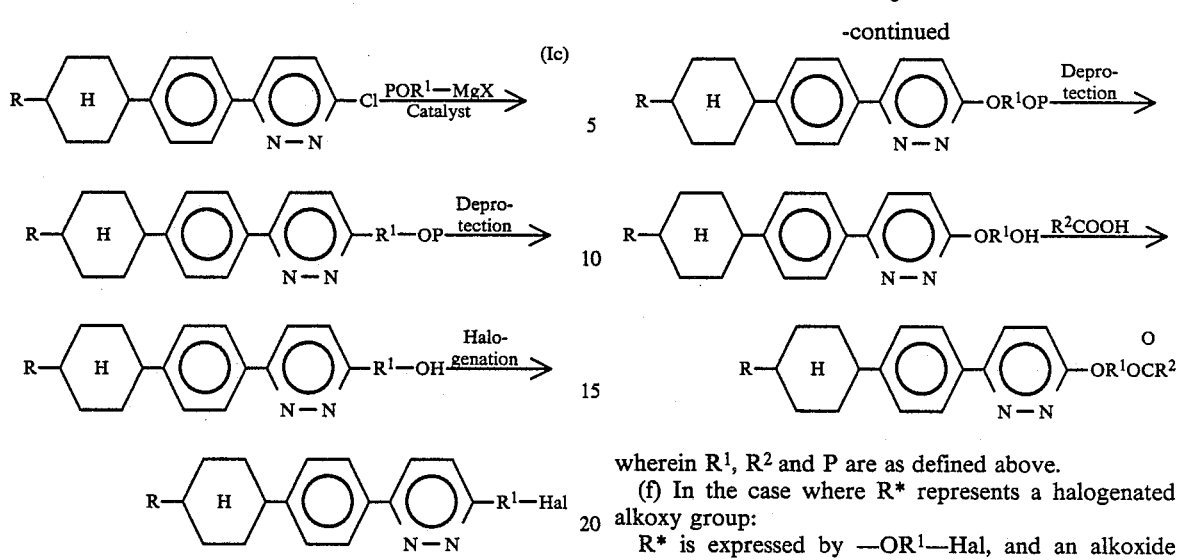

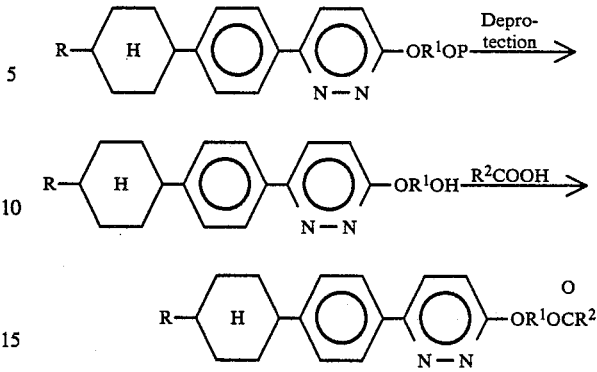

wherein X, the catalyst, P and $R^1$ are the same as the above, and Hal represents a halogen atom.

When the halogen atom is fluorine, the halogenation process therefor includes a process of once converting the alcohol into a sulfonic acid ester, followed by reacting KF, a process of using FAR (fluorinated amine reagent), a process of using DAST (diethylaminosulfur trifluoride), etc.

Further, when the halogen atom is chlorine, halogenating agents such as thionyl chloride, phosphorus oxychloride, phosphorus trichloride, phosphorus pentachloride, etc. are utilized. When the halogen atom is bromine, halogenating agents such as thionyl bromide, phosphorus tribromide, etc. are utilized.

(d) In the case where R* represents an alkoxy group or an alkoxyalkoxy group:

R* is expressed by the formula $R^*=R^{3*}O-$, and the following reaction is carried out:

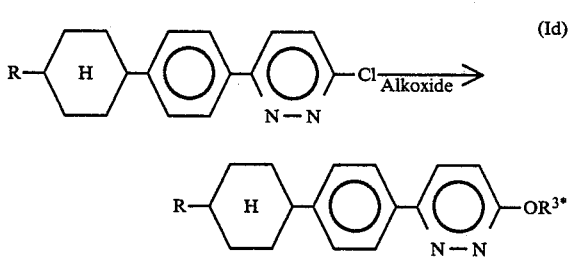

(e) In the case where R* represents an alkanoylalkoxy group:

R* is expressed by

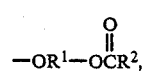

and an alkoxide prepared from $POR^1OH$ as its precursor is reacted as follows:

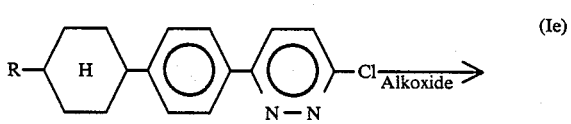

wherein $R^1$, $R^2$ and P are as defined above.

(f) In the case where R* represents a halogenated alkoxy group:

R* is expressed by $-OR^1$—Hal, and an alkoxide prepared from $POR^1OH$ as its precursor is reacted as follows:

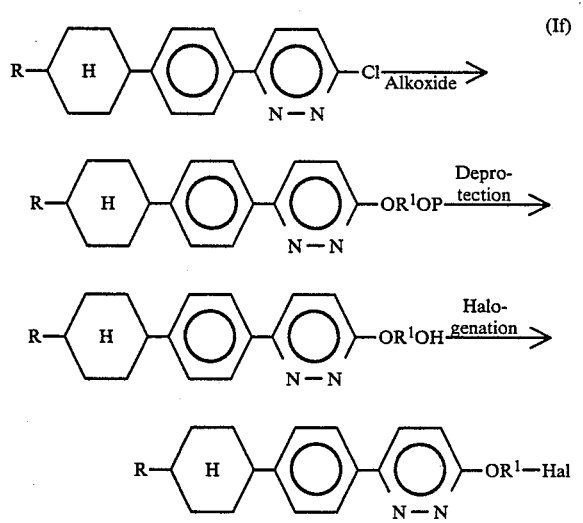

wherein $R^1$, P and Hal are as defined above.

As the R* group, the following groups may be concretely mentioned:

optically active alkyl groups such as 2-methylbutyl, 3-methylpentyl, 4-methylhexyl, 5-methylheptyl, 6-methyloctyl, 2-methylpentyl, 2-methylhexyl, 2-methylheptyl, 2-methyloctyl, 2-methylnonyl, 2-methyldecyl, etc., optically active alkoxy groups such as 1-methylpropoxy, 1-methylbutoxy, 1-methylpentoxy, 1-methylhexyloxy, 1-methylheptyloxy, 1-methyloctyloxy, 2-methylbutoxy, 2-methylpentoxy, 2-methylhexyloxy, 2-methylheptyloxy, 2-methyloctyloxy, 2-methylnonyloxy, 3-methylpentoxy, 4-methylhexyloxy, 5-methylheptyloxy, 6-methyloctyloxy, etc., alkoxyalkyl and alkoxyalkoxy groups such as 2-methoxypropyl, 2-ethoxypropyl, 2-propoxypropyl, 2-butoxypropyl, 2-pentoxypropyl, 2-hexyloxypropyl, 2-pentyloxypropyl, 2-methoxypropoxy, 2-ethoxypropoxy, 2-propoxypropoxy, 2-butoxypropoxy, 2-pentoxypropoxy, 1-methyl-2-methoxyethoxy, 1-methyl-2-ethoxyethoxy, 1-methyl-2-propoxyethoxy, 1-methyl-2-butoxyethoxy, 2-methyl-3-methoxypropyl, 2-methyl-3-ethoxypropoxy, etc., alkanoyloxalkyl groups such as 1-butanoyloxy-2-propyl, 1-(2'-methylbutanoyloxy)-2-propyl, 2-pentanoyloxy-1-propyl, 3-butanoyloxy-1-butyl, etc., alkanoyloxyalkoxy groups such as 1-propanoyloxy-2-propoxy, 1-(4'-methylhexanoyloxy)-2-propoxy, 2-butanoyloxy-1-propoxy, 2-(3'-methylpentanoyloxy)-1-propoxy, 3-propanoyloxy-1-butoxy, etc., halogenated alkyl groups such as 2-fluoro-octyl, 2-fluoro-propyl, 2-chloro-propyl, etc., halogenated alkoxy groups such as 2-fluoro-propoxy, 2-fluoro-4-methylpentyloxy, 2-fluoro-octyloxy, 2-chloro-propoxy, etc.

The liquid crystalline compound and liquid crystal composition of the present invention will be described in more detail by way of Examples.

EXAMPLE 1

Preparation of S-3-(2'-methylbutyloxy)-6-(4"-pentyl-trans-cyclohexyl-4'-phenyl)-pyridazine (a compound of the formula (I) wherein R represents pentyl and R* represents 2-methylbutyloxy)

(i) Preparation of 3-(4'-pentyl-cyclohexyl-benzoyl)-propanoic acid

A mixture of 4-pentyl-cyclohexyl-benzene (a mixture of cis and trans type compounds in equal quantities) (71 g, 0.31 mol), ground succinic anhydride (33 g, 0.33 mol) and carbon disulfide (400 ml) was cooled down to 0° to 5° C. with ice, followed by gradually adding ground anhydrous aluminum chloride (89 g, 0.67 mol), removing the ice bath used, returning the temperature to room temperature, agitating the mixture for one hour, successively agitating it on a water bath at 60° C. for 2 hours, allowing it to stand overnight, pouring the reaction mixture in a mixture of ice (300 g) with 6N-hydrochloric acid (50 ml), sufficiently agitating the mixture, distilling off carbon disulfide and water therefrom on a water bath, adding toluene (1 l), heating the mixture under reflux, separating water by means of a water separator of Dien-Stoke type, filtering the resulting material while hot, recrystallizing it in a refrigerator and filtering off crystals to obtain crystals (30 g). This product was 3-(4'-pentyl-trans-cyclohexyl-benzoyl)-propanoic acid.

(ii) Preparation of 3-(4"-pentyl-trans-cyclohexyl-4'-phenyl)-4,5-dihydro-pyridaz-6-one A mixture of 3-(4'-pentyl-trans-cyclohexyl-benzoyl)-propanoic acid (30 g), 80% hydrazine hydrate (30 g) and water (200 ml) was agitated on a water bath at 60° C. After a while, crystals formed in the vessel to make agitation impossible. Then ethanol (200 ml) was added and the mixture was agitated further for one hour, followed by allowing the resulting mixture to cool down to room temperature, filtering off the resulting crystals and recrystallizing the crystal form a mixture of ethyl acetate (300 ml) with ethanol (100 ml) to obtain 3-(4"-pentyl-trans-cyclohexyl-4'-phenyl)-4,5-dihydro-pyridaz-6-one (17 g). This product had a m.p. of 191.1° C., exhibited smectic A phase and constituted an isotropic liquid at 227°~229° C.

(iii) Preparation of 3-(4"-pentyl-trans-cyclohexyl-4'-phenyl)-pyridaz-6-one

While a mixture of 3-(4"-pentyl-trans-cyclohexyl-4'-phenyl)-4,5-dihydro-pyridaz-6-one (17 g) obtained in the above item (ii) with acetic acid (200 ml) was agitated on a water bath at 80° C., bromine (10 g) dissolved in acetic acid (80 ml) was slowly dropwise added to the mixture. When the solution was colored by the red color of bromine midway during the dropping, the dropping of bromine was completed. The solution was then allowed to cool down to room temperature. As a result, solids formed in the vessel, followed by filtering off the solids and recrystallizing from ethanol to obtain 3-(4"-pentyl-trans-cyclohexyl-4'-phenyl)-pyridaz-6-one (16 g). This product had a m.p. of 210.4° C., exhibited smectic A phase and constituted an isotropic liquid at 244°~246° C.

(iv) Preparation of 3-chloro-6-(4"-pentyl-trans-cyclohexyl-4'-phenyl)pyridazine

A mixture of 3-(4"-pentyl-trans-cyclohexyl-4'-phenyl)-pyridaz-6-one (16 g) obtained in the above item (iii), phosphorus oxychloride (45 ml) and N,N-diethylaniline (1 ml) was heated under reflux for 3 hours, followed by distilling off excess phosphorus oxychloride under reduced pressure, pouring the residue in ice, filtering off the resulting solids and recrystallizing from ethanol to obtain 3-chloro-6-(4"-pentyl-trans-cyclohexyl-4'-phenyl)-pyridazine (9 g). This product had a m.p. of 187.7° C., exhibited smectic A phase, transitted to nematic phase at 216° C. and constituted an isotropic liquid at 240° C.

(v) Preparation of the captioned compound

To a suspension of sodium hydride (about 55%) (0.4 g) in toluene (50 ml) was dropwise added a solution of S-(−)-2-methylbutanol (2 g) in toluene (20 ml), followed by heating the mixture under reflux for 30 minutes, allowing it to cool down to room temperature, thereafter feeding 3-chloro-6-(4"-pentyl-trans-cyclohexyl-4'-phenyl)-pyridazine (1.5 g) obtained in the above item (iv) in the form of solids as it is, thereinto, heating the mixture under reflux for 3 hours, pouring water in the rection liquid, heating the mixture under reflux for 3 hours, pouring water in the reaction liquid, washing the resulting organic layer with an alkali aqueous solution, then with an acid aqueous solution and further with water, drying with MgSO$_4$, distilling off the solvent, purifying the residue according to column chromatography using activated alumina (20 g) and toluene as an elute and recrystallizing from ethyl acetate to obtain the objective captioned S-3-(2'-methylbutyloxy)-6-(4"-pentyl-trans-cyclohexyl-4'-phenyl)-pyridazine (0.8 g). This product had a m.p. of 177.2° C., exhibited smectic A phase and constituted an isotropic liquid at 177.4° C.

EXAMPLE 2

Preparation of R-3-(1'-methylheptyloxy)-6-(4"-pentyl-trans-cyclohexyl-4'-phenyl)-pyridazine (a compound of the formula (I) wherein R represents pentyl and R* represents 1-methylheptyloxy) Using 3-chloro-6-(4"-pentyl-trans-cyclohexyl-4'-phenyl)-pyridazine (1.5 g) prepared in the item (iv) of Example 1, R-(−)-2-octanol (0.9 g) and sodium hydride (0.4 g), reaction, post-treatment and purification were carried out in the same manner as in Example 1—(v) to obtain the captioned R-3-(1-methylheptyloxy)-6-(4"-pentyl-trans-cyclohexyl)-pyridazine (0.7 g). This product had a m.p. of 116°~117° C.

EXAMPLE 3

Preparation of S-3-(4'-methylhexyloxy)-6-(4"-pentyl-cyclohexyl-4'-phenyl)-pyridazine (a compound of the formula (I) wherein R represents pentyl and R* represents 4-methylhexyloxy)

Using 3-chloro-6-(4"-pentyl-trans-cyclohexyl-4'-phenyl)pyridazine (1.5 g) prepared in Example 1—(iv), S-4-methylhexanol (2.0 g) and sodium hydride (0.4 g), reaction, post-treatment and purification were carried out in the same manner as in Example 1—(v) to obtain the captioned S-3-(4'-methylhexyloxy)-6-(4'''-pentyl-cyclohexyl-4'-phenyl)-pyridazine (0.7 g). This product had a m.p. of 151° C., exhibited smectic A phase and constituted an isotropic liquid at 179.5° C.

EXAMPLE 4

Preparation of S-3-(1'-methyl-2'-butoxyethoxy)-6-(4''-pentyl-cyclohexyl-4'-phenyl)-pyridazine (a compound of the formula (I) wherein R represents pentyl and R* represents 1-methyl-2-butoxyethoxy)

Using 3-chloro-6-(4''-pentyl-trans-cyclohexyl-4'-phenyl)-pyridazine (1.5 g) prepared in Example 1—(iv), S-1-butoxy-propan-2-ol (1.5 g) and sodium hydride (0.4 g), reaction, post-treatment and purification were carried out in the same manner as in Example 1—(v) to obtain the captioned S-3-(1'-methyl-2'-butoxyethoxy)-6-(4''-pentyl-cyclohexyl-4'-phenyl)-pyridazine (0.5 g). This product had a m.p. of 114° C., exhibited smectic A phase and constituted an isotropic liquid at 125° C.

EXAMPLE 5 (Use example)

A nematic liquid crystal composition consisting of

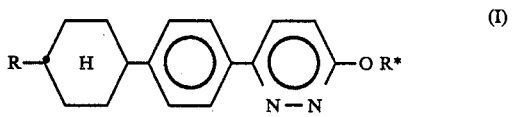

20 wt. %

40 wt. %

25 wt. %

15 wt. % was filled in a cell having a gap between electrodes of 10 μm to prepare a TN type display cell. When this cell was observed under a polarizing microscope, a reverse twist domain was observed to be formed. In addition, the cell used was subjected to a parallel aligning treatment by applying polyvinyl alcohol as an agent for aligning treatment and rubbing the resulting surface.

To the above nematic liquid crystal composition was added the compound of Example 4 as one of the compounds of the present invention, i.e.

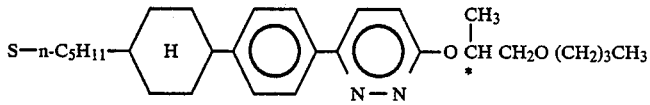

in a quantity of 0.5% by weight and the resulting composition was observed with a similar TN type cell. As a result, the reverse twist domain was dissolved and a uniform nematic phase was observed.

EXAMPLE 6 (Use example)

To a commercially available liquid crystal composition (ZLI-1132, tradename of a product made by Merck Co.) was added the compound of Example 2 in a quantity of 1% by weight to a chiral nematic liquid crystal composition. Its chiral pitch was measured according to Cano wedge method. The results were as follows:

| Temperature (°C.) | Pitch (μm) |
|---|---|
| 20 | 23.0 |
| 30 | 22.4 |
| 40 | 21.9 |
| 50 | 21.8 |
| 60 | 21.7 |
| 70 | 21.4 |

What we claim is:

1. A compound expressed by the formula (I)

R—⟨H⟩—⟨○⟩—⟨○⟩—O R*
                    N—N wherein R represents a normal alkyl group of 5-7 carbon atoms and R* represents an optically active alkyl or alkoxyalkyl group each of which has 5-8 carbon atoms with one methyl branching.

2. A compound according to claim 1 wherein said R* represents an optically active alkyl group of 5-8 carbon atoms with one methyl branching.

3. A compound according to claim 1 wherein said R* represents an optically active alkoxyalkyl group of 5-8 carbon atoms with one methyl branching.

4. A liquid crystal composition comprising at least two components at least one of which is a compound as set forth in claim 1.

* * * * *